United States Patent [19]

Cordon et al.

[11] 4,170,634
[45] Oct. 9, 1979

[54] MODIFIED ABRASIVE SYSTEM FOR DENTIFRICES

[75] Inventors: Martin Cordon, Highland Park; James Norfleet, Plainfield, both of N.J.

[73] Assignee: Colgate Palmolive Company, New York, N.Y.

[21] Appl. No.: 759,617

[22] Filed: Jan. 17, 1977

[30] Foreign Application Priority Data

Jan. 21, 1976 [AU] Australia .............................. 10444/76

[51] Int. Cl.$^2$ ......................... A61K 7/16; A61K 7/18
[52] U.S. Cl. ...................................... 424/49; 424/52; 424/54; 424/56; 424/57
[58] Field of Search .................................. 424/49–58; 51/309

Related U.S. Application Data

[63] Continuation-in-part of Ser. No. 544,618, Jan. 28, 1975, abandoned.

[56] References Cited

U.S. PATENT DOCUMENTS

| | | | |
|---|---|---|---|
| 2,393,844 | 1/1946 | van Valkenburgh | 51/309 |
| 2,550,207 | 4/1951 | Tainter et al. | 424/49 |
| 2,955,031 | 10/1960 | Bliton et al. | 51/309 |
| 3,003,919 | 10/1961 | Broge | 424/49 |
| 3,060,098 | 10/1962 | Gershon | 51/309 |
| 3,079,243 | 2/1963 | Veltz | 51/309 |
| 3,095,356 | 6/1963 | Moss | 424/52 X |
| 3,121,623 | 2/1964 | Nesin | 51/293 |
| 3,227,521 | 1/1966 | Carithers et al. | 23/142 |
| 3,325,368 | 6/1967 | Wood | 424/56 X |
| 3,622,622 | 11/1971 | Roberts et al. | 424/54 |
| 3,670,076 | 6/1972 | Muhler | 424/49 X |
| 3,678,155 | 6/1972 | Clippendale et al. | 424/52 |
| 3,728,446 | 4/1973 | Roberts et al. | 424/49 |
| 3,803,301 | 4/1974 | Cordon et al. | 424/49 |
| 3,822,345 | 7/1974 | Murray et al. | 424/52 |
| 3,929,987 | 12/1975 | Colodney et al. | 424/52 |
| 3,935,305 | 1/1976 | Delaney et al. | 424/49 |
| 3,943,240 | 3/1976 | Delaney et al. | 424/49 |
| 4,022,880 | 5/1977 | Vinson et al. | 424/49 |
| 4,048,300 | 9/1977 | Tomlinson et al. | 424/52 |

OTHER PUBLICATIONS

C.A. 78 #115218e (1973); C.A. 78 #75857d (1973); C.A. 77 #143745x (1972); C.A. 74 #6392d (1971).
C.A. 82 #6435s (1975); C.A. 72 #15769t (1970); C.A. 77 #66218y (1972); C.A. 79 #9779z (1973).

*Primary Examiner*—Shep K. Rose
*Attorney, Agent, or Firm*—Robert L. Stone; Murray M. Grill; Herbert S. Sylvester

[57] ABSTRACT

Dentifrice possessing superior cleaning and polishing characteristics containing as the essential ingredients at least one hard abrasive in an amount to provide a radioactive enamel abrasion to the dentifrice of above about 400, such as calcined alumina, zirconium silicate, and the like, and a non-toxic zinc compound in an amount to provide at least about 0.0065% by weight of zinc to the dentifrice.

6 Claims, No Drawings

MODIFIED ABRASIVE SYSTEM FOR DENTIFRICES

This application is a Continuation in Part of copending patent application Ser. no. 544,618 filed Jan. 28, 1975 now abandoned.

This invention relates to a dentifrice having superior cleaning and polishing characteristics containing at least one hard abrasive having a particle size of about 1 to 15 microns in diameter, and in an amount to provide a radioactive enamel abrasion value (REA) above about 400 to the dentifrice, said hard abrasive being preferably present in an amount of at least about 7.5% by weight of said dentifrice; and a non-toxic zinc compound in an amount to provide at least about 0.0065% by weight of zinc to the dentifrice, to reduce the aforesaid radioactive enamel abrasion of the composition.

It has been difficult heretofore to provide dentifrices for use in the daily brushing and cleaning of teeth which provide a desirable balance of cleaning and polishing action. This has been largely due to the difficulty in selecting suitable abrasives which will afford maximum removal of difficult stains and debris without damaging the enamel surfaces of the teeth.

The function of an abrasive substance in formulations intended for use in the oral cavity is to remove various deposits, including pellicle film from the surface of the teeth. Pellicle film is a tightly adherent film which often contains brown or yellow pigments and imparts an unsightly appearance to the teeth. An advantageous abrasive material for incorporation into dental formulations should maximize film removal without causing undue abrasion to the hard tooth tissues. The typical soft abrasive used in dental compositions, such as dicalcium phosphate and calcium pyrophosphate, although not unduly abrasive to tooth tissue, are not as effective as the hard abrasives in removing these undesirable deposits from the teeth. However, hard abrasives can present serious problems when present in dental preparations since their outstanding abrasive characteristics are likely to cause undue abrasion to the oral hard tissues (enamel, dentin and cementum).

It has now been found that the addition of a non-toxic zinc compound in an amount to provide at least about 0.0065% by weight of zinc, to a dental abrasive system containing at least one hard abrasive effects a substantial reduction in the radioactive enamel abrasion thereof. This is a particularly desirable feature when applied to the group of abrasives known as hard abrasives. Dentifrice formulations can now be made containing hard abrasives (heretofore relatively undesirable because of their tendency to abrade tooth enamel) to give superior polishing and cleaning without encountering undue enamel abrasion.

Accordingly, a dentifrice possessing superior cleaning and polishing action without increasing the enamel abrasivity thereof can be formulated comprising small amounts of a non-toxic zinc compound, and at least one hard abrasive having a particle size of about 1 to 15 microns in diameter and in an amount to provide a radioactive enamel abrasion value (REA) above about 400.

The non-toxic zinc compounds found to be effective in reducing the radioactive enamel abrasion of abrasive materials include zinc oxide and the water soluble zinc compounds, in amounts as low as 0.01% to about 2.0% by weight of the total formulation. Larger amounts may be utilized, although a maximum of 2.0% by weight is preferred. The zinc compounds found particularly effective may be selected from the group consisting of zinc oxide, zinc chloride, zinc acetate, zinc sulfate and zinc nitrate. Although the zinc compounds substantially reduced enamel abrasion, it had little effect on dentin abrasion.

Hard, inorganic, mineral-like substances, well known for their abrasive properties, are not generally suitable per se as dentifrice cleaning agents because they are too abrasive. However, a certain class of hard particulate mineral-like substances provides effective cleaning and polishing, and their enamel abrasivity is minimized by the addition of a minor amount of a zinc compound. The inorganic mineral-like substance useful as hard dental abrasives herein should be capable of providing to a dentifrice an REA value above about 400 units, when present in an amount of at least about 7.5% by weight of said dentifrice, and should be in particulate form with a mean particle diameter in the range of about 1 micron to 15 microns and preferably about 2 to 10 microns, and be selected from the group consisting of crystalline silica, calcined alumina, zirconium silicate, feldspar ($KAlSi_3O_8$), grit (SiC), pumice, ilmenite ($FeTiO_3$), $CeO_2$, $Fe_2O_3$ (hematite), $ZrO_2$, $SnO_2$, and topaz (aluminum hydroxy fluorosilicate). The "hard abrasive" utilized herein may be defined as an abrasive capable of providing an REA value above about 400 to a dentifrice. Most commercial dentifrices presently on the market have an REA value up to about 300, and as low as 50. The preferred group of hard abrasives include calcined alumina, zirconium silicate, pumice, feldspar and zirconium oxide.

Calcined alumina is the preferred abrasive in this invention. Flaked calcined alumina is defined as flat flakes of alpha-alumina crystals, of disc- or plate-like configuration, said flakes having a mean (by weight) particle diameter of less than about 7 microns (e.g., about 2 to 7 microns). Viewed under a scanning electron microscope, the flat alumina particles have sharp edges indicating that they have been fractured perpendicular to their flat parallel faces. Generally, the thickness of the flat flakes are less than about ⅓ (e.g., about ⅛ to 1/10) of their diameters, and are in the range of about ½ micron (or less) to about 2 microns (e.g., about 1 micron). The flat alpha-alumina crystals and a process for preparing them are described in U.S. Pat. No. 3,121,623.

Another desirable grade of calcined alumina is composed of ground crystals of alpha-alumina, ground to its ultimate particles form and having a mean ultimate particle size of 1 to 2 microns, e.g., 1.6 microns.

The presence of the flat alpha-alumina particles or other hard abrasive particles is found to impart improved tooth polishing and tooth cleaning and stain removal characteristics to the dentifrice.

The proportion of the calcined alumina or other hard abrasive in the dentifrice may be, for instance, above 7.5% and in the range of about 7.5 to 20% preferably about 7.5 to 10%.

In addition to at least one hard abrasive, a sufficient amount of an additional dental abrasive may be included. Accordingly, the additional abrasive is soft in abrasiveness on enamel by comparison, and may be, for instance, any of those conventionally employed in toothpastes, such as hydrated alumina, anhydrous dicalcium phosphate, insoluble sodium metaphosphate, dicalcium phosphate dihydrate, calcium carbonate, silica xerogels of the known high density or intermediate density types (such as those sold under the name Syloid 63 or Syloid 72 or Syloid 74, amorphous alkali metal or alkaline earth metal alumino-silicates (such as those having a refractive index of about 1.44–1.47, and containing at least about 70% silica, up to about 10% alumina, up to about 20% by weight of moisture and up to about 10% by weight of sodium oxide, the moisture content preferably being about 10–20% by weight, measured by loss at 1000° C. and the typical content of sodium oxide being about 5–10% by weight), kappa-alumina (such as described in U.S. Pat. No. 3,003,919); synthetic resins (such as described in British Pat. No. 995,351); composite abrasive particles in which a hard mineral is coated with, or embedded in, a synthetic resin (the mineral being, for instance, crystalline silica, e.g., quartz, SiC, anhydrous alumina, hematite, zirconium silicate, etc., and the coating being, for instance, an impervious cross-linked thermoset synthetic resin such as melamine-formaldehyde resin, urea-formaldehyde, phenol-formaldehyde, or epoxy resins or polymers or copolymers of compounds having two or more polymerizable ethylenically unsaturated groups, e.g., diallyl phthalate polymers, such as described in U.S. Pat. No. 3,151,027).

The soft dental abrasive may have a particle size about 2 to 40 microns and may also be present in the form of relatively large agglomerates (of the individual particles) of such size as to be visible to the naked eye but easily reduced to the fine impalpable particle size upon being subjected to tooth-brushing in the mouth. Such agglomerates may be agglomerated with or without binding agent which may be water-soluble or water insoluble.

For most purposes it is preferable that the soft dental abrasive have a particle size less than 20 microns to avoid any gritty feel.

The proportion of such additional dental abrasive in the dentifrice is usually in the range of about 10 to 50%, and is preferably such that when the alpha alumina or other hard abrasive is omitted from the dentifrice, the RDA (radioactive dentin abrasion) is in the range of about 100 to 600, preferably about 100 or 200 to 450. Typically, this proportion of dental abrasive is in the range of about 5 to 70% of the dentifrice, and preferably about 10 to 50%.

It is also within the broader scope of this invention to employ the alpha-alumina flakes as the sole abrasive in the dentifrice, e.g., in concentrations of about 10 to 20%. In this case, it is often desirable to include other solid ingredients such as inorganic fillers and/or the finely divided thermoplastic polymers mentioned below, so as to provide a toothpaste of suitable consistency.

To make toothpastes or dental creams, the hard abrasive such as the flat flakes of alpha-alumina and any other dental abrasives are dispersed in a dental vehicle which preferably contains a liquid which is water and/or a humectant such as glycerine, sorbitol, xylitol, propylene glycol or polyethylene glycol 400, including suitable mixtures thereof. It is usually advantageous to use a mixture of both water and one or two humeotants. Polyethylene glycols of higher molecular weight, e.g., polyethylene glycol 600 etc., may also be present. The total liquid content is generally well over 20% by weight of the vehicle (sorbitol, generally present in admixture with water, is considered as a liquid for this purpose). The preferred humectants are glycerine and sorbitol. Typically, the vehicle contains about 0–80% by weight of glycerine, up to about 80% by weight of sorbitol and about 5–80% of water.

The zinc compound may be added directly to the dental vehicle containing the abrasives, or the abrasives may be pretreated with the zinc compound particularly with the water-soluble zinc salts such as zinc chloride, zinc sulfate, zinc acetate, and zinc nitrate, and the pretreated abrasives added to a suitable dental vehicle. The zinc oxide is typically added directly to the vehicle along with the abrasives because of its water-insolubility. The zinc chloride, zinc sulfate, zinc acetate or zinc nitrate being water-soluble, is preferably dissolved in an aqueous solution and stirred with the abrasive (typically both the hard and soft abrasive, if both used in the dentifrice). The solids are then isolated and washed twice with water. The zinc pretreated abrasive is then incorporated into a dental vehicle. The unique reduction in enamel abrasiveness is the result of the combination of zinc compound and abrasive. When the abrasive is pretreated with the water soluble zinc salt, substantially similar large reductions in enamel abrasivity of the finished dentifrices are observed with varying concentrations of zinc in the dentifrices. When the hard abrasives and zinc compound, particularly zinc oxide, are separately incorporated into the dentifrices, reductions in enamel abrasivity are increased with greater concentrations of zinc in the dentifrices.

The vehicle usually also contains a thickening or gelling agent, such as the natural and synthetic gums and gum-like materials, such as Irish Moss, gum tragacanth, alkali metal (e.g., Li, K or Na) carboxymethyl cellulose and hydroxymethyl carboxyethyl cellulose, polyvinyl pyrrolidone, starch, xylitol, water-soluble hydrophilic colloidal carboxyvinyl polymers such as those sold under the trademark Carbopol 934 and 940, hydroxyethyl cellulose, Indian gum, acacia gums, agar agar, locust bean gum, Laponite CP or SP, which are each synthetic inorganic complex silicate clays sold under trademark by Laporte Industries, Ltd., and pectin or inorganic thickeners such as colloidal silica, e.g., synthetic finely divided silicas including those sold under the trademarks Cab-O-Sil M5, Syloid 244, Syloid 266, Zeosyl 200 and Aerosil D200. The solid portion of the vehicle is typically present in an amount up to about 10% by weight of the toothpaste and preferably within the range of about 0.5–8% by weight.

Fine particles of thermoplastic resin may also be present, such as particles of solid polymer having a molecular weight above 1000 (and preferably above 10,000, e.g., about 10,000 to 100,000 or more) and a mean diameter less than about 50 microns (preferably in the range of about 0.5 to 50 microns, e.g., about 10 to 30 microns). The polymer particles may be prepared directly by emulsion or suspension polymerizing or by grinding the polymer in bulk, and may be present in amount of up to about 60% or more of the dentifrice, e.g., in the range of about 20 to 60%, such as about 20 to 50%, e.g., about 30 to 50% in a toothpaste. Examples of thermoplastic resins are polymerized ethylenically unsaturated compounds, such as polyolefines (e.g., polyethylene or polypropylene) or vinyl or vinylidene resins, such as polyvinyl chloride, polystyrene, vinyl chloride-vinyl acetate copolymers, styrene-butadiene copolymers, polyvinylidene chloride; polyamides such as Nylon (e.g., Nylon 6); cellulosics such as cellulose acetate, etc.

The toothpaste may also contain surface-active agent, e.g., to achieve increased prophylactic action, assist in achieving thorough and complete dispersion of the instant compositions throughout the oral cavity, and render the instant compositions more cosmetically acceptable. The organic surface-active material may be anionic, nonionic, ampholytic, or cationic in nature, and it is preferred to employ as the surface-active agent a detersive material which imparts to the composition detersive and foaming properties. Suitable types of such detergents are water soluble salts of higher fatty acid monoglyceride monosulfates, such as sodium salt of the monosulfated monoglyceride or hydrogenated coconut oil fatty acids, higher alkyl sulfates, such as sodium lauryl sulfate, alkyl aryl sulfonates, such as sodium dodecyl benzene sulfonate, higher alkyl sulfoacetates, higher fatty acid ester of 1,2 hydroxy propane sulfonates, and the substantially saturated higher aliphatic acyl amides of lower aliphatic amino carboxylic acid compounds, such as those having 12 to 16 carbons in the fatty acid alkyl or acyl radicals and the like. Examples of the last-mentioned amides are N-lauroyl sarcosine, and the sodium, potassium, and ethanolamine salts of N-lauroyl, N-myristyl or N-palmityl sarcosinates, which should be substantially free from soap or similar higher fatty acid material which tends to substantially reduce the effect of these compounds. The use of these sarcosinate compounds in dentifrice compositions of the present invention is particularly advantageous since these materials exhibit a prolonged and marked effect in the inhibition of acid in the oral cavity due to carbohydrates, in addition to exerting some reduction in the solubility of tooth enamel in acid solutions.

Other suitable surface active materials include non-ionic agents such as condensates of sorbitan monostearate with approximately 60 moles of ethylene oxide, condensates of ethylene oxide with propylene oxide, condensates of propylene glycol ("Pluronics"), and cationic surface active germicides and antibacterial compounds such as di-isobutylphenoxyethyldimethyl benzyl ammonium chloride, benzyl dimethyl stearyl ammonium chloride, tertiary amines having one fatty alkyl group (of from 12 to 18 carbon atoms) and two (poly) ethylene groups attached to the nitrogen (typically containing a total of from about 2 to 50 ethenoxy groups per molecule) and salts thereof with acids, and compounds of the structure;

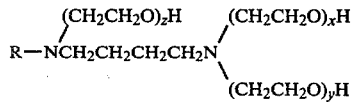

where R is a fatty alkyl group containing from about 12 to 18 carbon atoms, and x, y and z total 3 or higher, as well as salts thereof with mineral organic acids, may also be used. It is preferred that the total amount of surface-active agent be about 0.05–5% by weight, preferably about 1–3%, of the dentifrice.

Various other materials may be incorporated in the oral preparation of this invention. Examples thereof are coloring or whitening agents such as titanium dioxide, preservatives, silicones, chlorophyll compounds, ammoniated materials, such as urea, diammoniumphosphate and mixtures thereof, and other constituents. Each of these adjuvants may be typically incorporated in the instant toothpastes in amounts up to about 5%.

The toothpaste may also contain antibacterial agents in amounts of about 0.01–5%. Typical examples of such agents are guanidines, biguanides and amines such as:

$N^1$-(4-chlorobenzyl)-$N^5$-2,4-(dichlorobenzyl)biguanide;
p-chlorophenyl biguanide;
4-chlorobenzhydryl biguanide;
4-chlorobenzhydrylguanylurea;
$N^1$-3-lauroxypropyl-$N^5$-p-chlorobenzylbiguanide;
1,6-di-p-chlorophenylbiguanidohexane;
1-(lauryldimethylammonium)-8-(p-chlorobenzyldimethylammonium) octane dichloride;
5,6-dichloro-2-guanidinobenzimidazole;
$N^1$-p-chlorophenyl-$N^5$-laurylbiguanide;
5-amino-1, 3-bis(2-ethylhexyl)-5-methylhexahydropyrimidine; and their non-toxic acid addition salts.
Benzethonium chloride
Cetyl pyridinium chloride Suitable flavoring or sweetening sialagogues may be employed in formulating a flavor for the compositions of the present invention. Examples of suitable flavoring constituents include the flavoring oils, e.g., oils of spearmint, peppermint, winter-green, sassafras, clove, sage, eucalyptus, marjoram, cinnamon, lemon and orange, as well as methyl salicylate. Suitable sweetening agents include sucrose, lactose, maltose, sorbitol, xylitol, sodium cyclamate and saccharin. Suitably, flavor and sweetening agent may together comprise from about 0.01 to 5% more of the compositions of the instant invention.

The compositions of the present invention suitably may also contain a fluorine-containing compound having a beneficial effect on the care and hygiene of the oral cavity, e.g., diminution of enamel solubility in acid and protection of the teeth against decay. Examples thereof include sodium fluoride, stannous fluoride ($SnF_2KF$), sodium hexafluorostannate, stannous chlorofluoride sodium fluorozirconate and sodium monofluorophosphate. These materials, which dissociate or release fluorine-containing ions in water, suitably may be present in an effective but nontoxic amount, usually within the range of about 0.01 to 1% by weight of the water-soluble fluorine content thereof.

The dentifrice may be prepared by suitably mixing the ingredients. For instance in making a toothpaste, a gelling agent such as sodium carboxymethyl cellulose or Carbopol 934 and a preservative such as sodium benzoate, if employed, is dispersed with a humectant such as glycerine. Water may also be present. Additional humectant and water, as an aqueous 70% sorbitol solution, may then be mixed with the dispersion and a paste, gel or cream is formed. Dental abrasive agent, surface-active agent and flavor are then added. The toothpaste is then thoroughly deaerated (e.g., in vacuo) and tubed.

Preferably the amount of water-insoluble essential flavoring oil is above 0.5% and below 2%. Strongly flavored toothpastes contain above 1% of such flavoring oil, e.g., about 1.2 to 1.5%.

Instant formulations have been found useful as prophylactic dental pastes applied professionally, preparations for use on dentures and for daily use on the teeth.

The following examples are given to illustrate this invention further. In this application all proportions are by weight unless otherwise indicated.

EXAMPLE 1

A toothpaste is prepared according to the following formulation: glycerine 25%; sodium carboxymethyl cellulose 1.2%; sodium benzoate 0.50%; sodium saccharin 0.20%; sodium alumino-silicate 24.0%; titanium dioxide 0.2%; zinc oxide 0.4%; calcined alumina ("Microgrit"-alpha-alumina flakes) 7.5%; sodium lauryl sulfate 1.5%; flavoring oil 1.00%; deionized water 38.5%. The alpha alumina flakes have a mean (by weight) particle diameter of about 4 microns, all the particles thereof have diameters less than 10.1 microns, about 85–95% (by weight) have diameters less than 6.0 microns and about 30–35% have particle diameters less than 3.5 microns. The sodium alumino-silicate contains 89–91% silica, 0.8–1.2% alumina and 0.3–0.9% sodium oxide. This toothpaste has an REA of 291, and an RDA value of 311. An otherwise identical toothpaste containing no zinc oxide has an REA of about 890; and an RDA value of 324.

REA represents the radioactive enamel abrasion value obtained by a technique described in the literature.

A method for determining enamel abrasion values for the agents is as follows: Molar teeth are exposed to neutron radiation whereby a predetermined portion of phosphate content is converted to $P^{32}$. Each enamel specimen is mounted in a self-curing polymer such as methyl methacrylate. The specimens are then placed in the specially designed apparatus consisting essentially of a means of stabilizing the enamel specimen, a tube to contain the diluted toothpaste and a toothbrush head under a tension of 150 grams. The enamel specimen is then subjected to 4500 reciprocal brush strokes over the cusped surface. A 2.0 ml aliquot is placed in a planchet, dried at room temperature, and the radioactivity ($P^{32}$) determined using a conventional Geiger-Mueller detector. By comparing the radioactivity of the slurries of the experimental pastes to that obtained on each enamel specimen with a reference, calcium pyrophosphate powder, which is arbitrarily assigned an enamel abrasion score of 500, the relative abrasiveness of the experimental pastes may be determined.

The RDA values may be suitably determined using the dentin portions separated from human cuspids and subjecting said dentin to 1000 reciprocal brush strokes. This radioactive technique is more fully described in the literature; Stookey, C. K. and Muhler, J. C., J. Dental Research 47 524–538 (1968). Similarly to the REA values, the dentin abrasion must likewise not be high in order to prevent or minimize oral hard tissue damage.

EXAMPLE 2

Example 1 is repeated except that the zinc oxide content is reduced to 0.2%, the calcined alumina is increased to 10%, the titanium dioxide is increased to 0.4% and the water is reduced to 36.0%. This toothpaste has an REA value of 265 and RDA value of 304.

EXAMPLE 3

Example 2 is repeated except that the zinc oxide is reduced to 0.1% and the water content adjusted accordingly. This product has an REA value of 300 and RDA value of 323.

EXAMPLE 4

Example 2 is repeated except that the zinc oxide is reduced to 0.05% and the water content adjusted accordingly. REA value of 335; RDA value of 321.

EXAMPLE 5

Example 2 is repeated, but the zinc oxide content is reduced to 0.03% and the water adjusted accordingly. This toothpaste has a REA value of 395; RDA value of 315.

EXAMPLE 6

Example 2 is repeated but the zinc oxide is reduced to 0.01% and the water content adjusted. This dentifrice has a REA value of 531; a RDA value of 338.

EXAMPLE 7

Example 2 is repeated but the zinc oxide is increased to 0.4% and the water is adjusted accordingly. This formulation has a REA value of 310 and a RDA value of 315.

Thus, it is apparent that zinc oxide in amounts as low as 0.01% by weight effectively reduces the enamel abrasivity of the formulation within acceptable commercial limits in the obtention of a superior cleaning and polishing dentifrice. It may also be noted that while there are very large reductions in enamel abrasion, there is little effect on dentin abrasion. In addition, the presence of zinc oxide (0.4%) increased the polishing effect of the dentifrice from 50% to 79% repolish.

EXAMPLE 8

10% zirconium silicate is substituted for the 10% calcined alumina in Example 7. This formulation has an REA value of 164 and RDA value of 254. An identical toothpaste without the zinc oxide had an REA value of 520 and an RDA value of 338.

EXAMPLE 9

Example 1 is repeated but 0.67% $ZnCl_2$ is substituted for the ZnO and the water is adjusted accordingly. This formulation has a REA value of 245 and a RDA value of 278, whereas a separately prepared composition without the $ZnCl_2$ has a 596 REA and a 362 RDA value.

EXAMPLE 10

The abrasive system consisting of the sodium alumino-silicate and calcined alumina of Example 2 is stirred with an aqueous solution containing 0.67% $ZnCl_2$ for five minutes. The pretreated abrasive system is separated from the aqueous solution, washed twice with water and then added to the rest of the ingredients of the composition of Example 1. The resultant REA value is 349 as against 606 in the absence of the pretreatment with $ZnCl_2$.

EXAMPLE 11

10% zirconium silicate may be substituted for the calcined alumina of Example 10 and the zinc chloride pretreated abrasive system incorporated into the dentifrice vehicle. This product also yields a beneficial reduction in the enamel abrasivity of said formulation.

EXAMPLE 12

Example 1 is repeated except that the calcined alumina content is increased to 10% and 1.42% zinc sulfate is used in lieu of the 0.4% zinc oxide. This formulation has a REA value of 258, whereas a separately prepared composition without the zinc sulfate has a 575 REA value.

EXAMPLE 13

10% zirconium silicate may be substituted for the calcined alumina of Example 12. This product also yields a beneficial reduction in the enamel abrasivity of said formulation.

EXAMPLE 14

Example 12 is repeated except that 1.08% zinc acetate is substituted for the zinc sulfate. This formulation has a REA value of 299, whereas a separately prepared composition without the zinc acetate has a 575 REA value.

EXAMPLE 15

Example 12 is repeated except that 10% pumice powder is substituted for the 10% calcined alumina and 0.67% zinc chloride is used in lieu of the 0.4% zinc oxide. This formulation has an REA value of 667, whereas a separately prepared composition without the zinc chloride has a REA value of 1275. Thus, it is apparant that the presence of a small amount of zinc chloride was effective in reducing the abrasivity of the pumice-containing abrasive to about one-half of its original value.

EXAMPLE 16

Example 15 is repeated except that 10% feldspar (KAl-$Si_3O_8$) is substituted for the 10% pumice powder. This formulation has a REA value of 433, whereas a separately prepared composition without the zinc chloride has a REA value of 974.

EXAMPLE 17

Example 15 is repeated except that 10% $ZrO_2$ is substituted for the 10% pumice powder. This formulation has a REA value of 122, whereas a separately prepared composition without the zinc chloride has an REA value of 450.

It is also within the broader scope of the invention to include other alpha aluminas and/or other hard abrasives, in admixture with dental abrasives other than sodium alumino-silicate, such as the insoluble calcium and sodium phosphates, carbonates and other aforementioned softer abrasives.

An example of another calcined alumina is a pulverized alpha-alumina of irregular shape and having a mean particle size of about 3 to 4 microns (with all said irregular particles being less than about 7 microns in their largest dimension).

While the alpha-alumina flakes or other hard abrasive have proved most useful thus far in toothpastes, they may also be similarly incorporated into toothpowders or into dental creams which are of pourable consistency.

The pH of the dentifrices is generally within the range of about 4 to 10, e.g., about 5 to 8.

The particle diameters given in the examples are determined by conventional methods. Thus, the standard liquid sedimentation technique may be used. The calculation of particle diameter from the sedimentation data being made (as is conventional) on the basis of Stokes' Law, disregarding the particular shape of the particles.

The alpha-alumina flakes used in Example 1 are sold under the name "MICROGRIT".

It is understood that the foregoing detailed description is given merely by way of illustration and that variations may be made therein without departing from the spirit of the invention. The "Abstract" given above is merely for the convenience of technical searchers and is not to be given any weight with respect to the scope of the invention.

We claim:

1. A dentifrice of superior cleaning and polishing characteristics containing as the essential ingredients, an abrasive system having at least one soft abrasive and including a hard abrasive having a particle size of about 1 to 15 microns in diameter selected from the group consisting of calcined alumina, zirconium silicate, feldspar, pumice, and $ZrO_2$, and in an amount to provide a radioactive enamel abrasion value to the dentifrice of above about 400 and present in an amount of at least 7.5% and up to 20% by weight of the dentifrice, and a non-toxic zinc compound in an amount to provide at least about 0.0065% zinc to the dentifrice, said abrasive system being pretreated with a water-soluble zinc compound selected from the group consisting of zinc chloride, zinc sulfate, zinc acetate, zinc nitrate in an amount of about 0.01-2.0% by weight of the dentifrice, so as to reduce the enamel abrasion of the dentifrice.

2. A dentifrice as in claim 1 in which said hard abrasive is calcined alumina in the form of alpha alumina flakes having an average diameter in the range of 2 to 7 microns.

3. A dentifrice as in claim 1 in which said hard abrasive is zirconium silicate.

4. A dentifrice as in claim 1 in which the amount of said soft dental abrasive is in the range of about 10 to 50% and the amount of said hard abrasive is about 7.5 to 20%.

5. A dentifrice as in claim 4, in which the soft abrasive is sodium alumino-silicate.

6. A dentifrice as in claim 1, wherein the hard abrasive is calcined alumina.

* * * * *